US00PP18760P3

(12) United States Plant Patent
Zwaan

(10) Patent No.: US PP18,760 P3
(45) Date of Patent: Apr. 29, 2008

(54) *ACHILLEA* PLANT NAMED 'WONDERFUL WAMPEE'

(50) Latin Name: *Achillea millefolium*
Varietal Denomination: Wonderful Wampee

(75) Inventor: Michiel Zwaan, Alphen aan den Rijn (NL)

(73) Assignee: K. Sahin, Alphen aan den Rijn (NL)

( * ) Notice: Subject to any disclaimer, the term of this patent is extended or adjusted under 35 U.S.C. 154(b) by 217 days.

(21) Appl. No.: 11/348,942

(22) Filed: Feb. 7, 2006

(65) Prior Publication Data

US 2007/0186321 P1 Aug. 9, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Penny J. Aguirre

(57) ABSTRACT

A new cultivar of *Achillea millefolium,* 'Wonderful Wampee', characterized by it long blooming habit, its vigorous growth habit, its compact growth habit and its bright clear pink flowers that fade to a light pink with consistent bloom color throughout the plant.

2 Drawing Sheets

Botanical classification: *Achillea millefolium.*
Variety denomination: 'Wonderful Wampee'.

CROSS REFERENCE TO A RELATED APPLICATION

This application is co-pending with U.S. Plant Patent application filed for a plant derived from the same breeding program entitled *Achillea* Plant Named 'Apricot Delight'. (U.S. Plant patent application Ser. No. 11/348,934).

BACKGROUND OF THE INVENTION

The present invention relates to a new and distinct cultivar of *Achillea* plant, botanically known as *Achillea millefolium* 'Wonderful Wampee' and will be referred to hereinafter by its cultivar name, 'Wonderful Wampee'. The new cultivar of *Achillea* is an herbaceous perennial grown for landscape use.

'Wonderful Wampee' was derived from a breeding program that focused on obtaining *Achillea* cultivars with a long blooming habit and flower colors that are resistant to fading. 'Wonderful Wampee' was selected in the summer of 2001 as a whole plant mutation that arose from repeated selections from seed originally sown of the seed strain *Achillea* 'Summer Pastels' (not patented) in Boskoop, The Netherlands.

'Wonderful Wampee' was selected as unique primarily for its sturdy stems, its compact plant habit and its clear pink flowers. 'Summer Pastels', the parent strain, produces plants with variable plant habits and flowers with variable colors and color-fastness. 'Wonderful Wampee' differs from its closest comparison cultivar based on flower color, *Achillea millefolium* 'Appleblossom' (not patented), in having a more compact plant habit. 'Wonderful Wampee' is more densely foliaged, has shorter stem internodes, and is shorter in height than 'Appleblossom'. 'Wonderful Wampee' is similar in bloom period and plant habit to 'Apricot Delight' from the same breeding program, however 'Apricot Delight' has salmon pink flowers and is slightly shorter.

Asexual reproduction of the new cultivar was first accomplished by basal cuttings in under the direction of the inventor in Lancaster, Pa. in September of 2002. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Wonderful Wampee' as unique from and all other varieties of *Achillea* known to the inventor.

1. 'Wonderful Wampee' is long blooming, blooming for about five weeks, typically from late June through July in Lancaster, Pa.
2. 'Wonderful Wampee' has clear pink flowers that are consistent in color and fade to a light pink.
3. 'Wonderful Wampee' is densely foliated with thick dark green foliage on short internodes resulting in a compact plant habit.
4. 'Wonderful Wampee' has a vigorous growth habit.

BRIEF DESCRIPTION OF THE DRAWINGS

The accompanying colored photographs illustrate the overall appearance and distinct characteristics of the new *Achillea.* The photographs represent two year-old plants as field grown in Lancaster, Pa.

Figure 1:
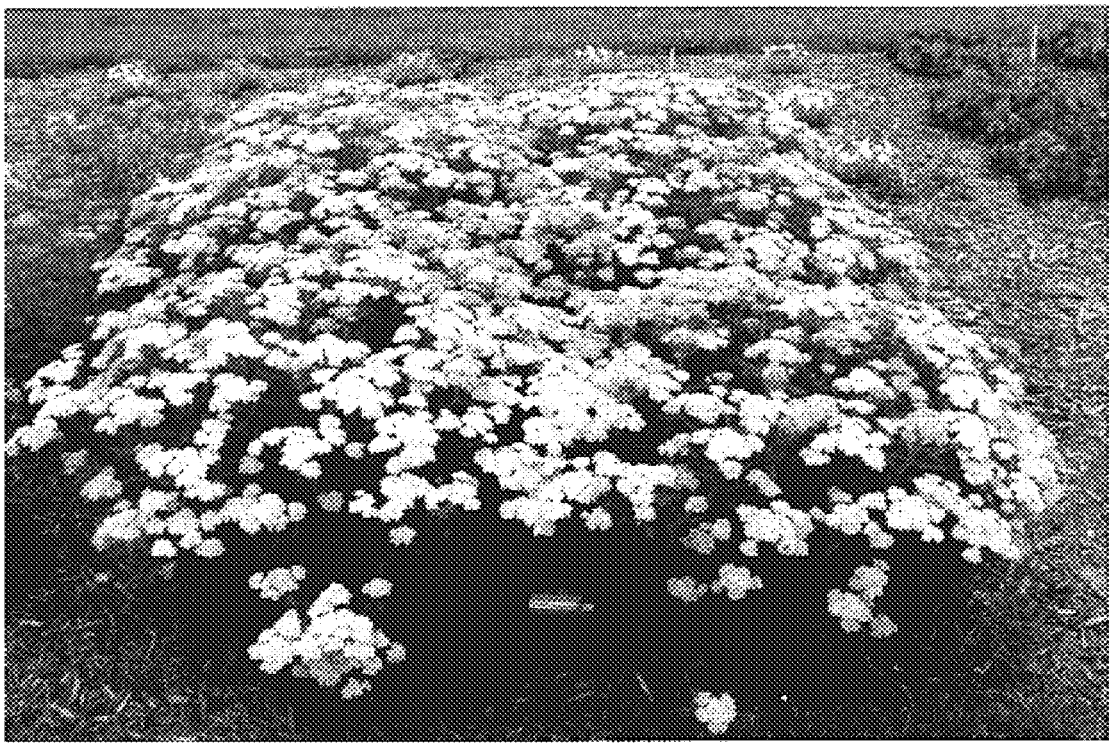
FIG. 1 is a photograph of a group of 'Wonderful Wampee' in bloom and shows the consistent and compact plant habit.
Figure 2:
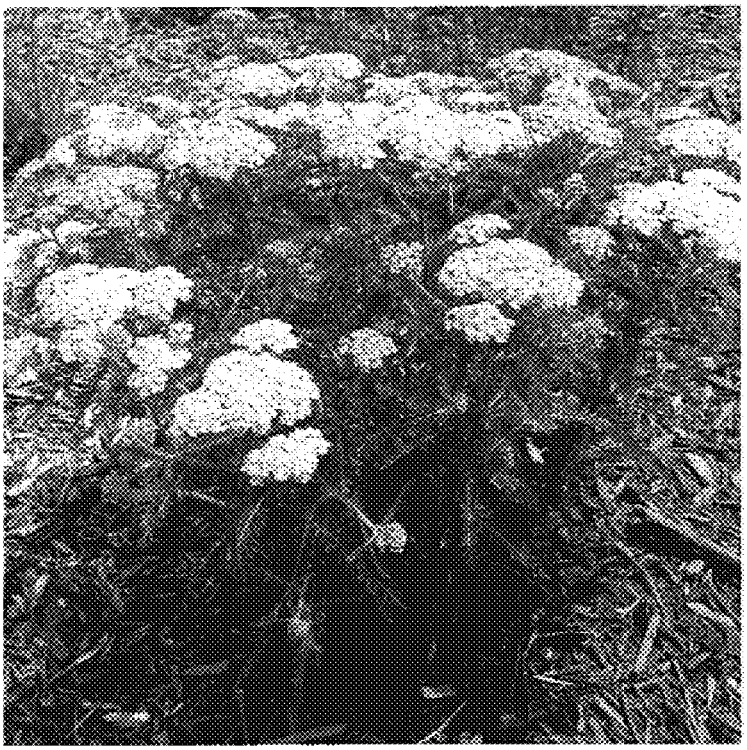
FIG. 2 is a photograph of a single plant of 'Wonderful Wampee'.
Figure 3:
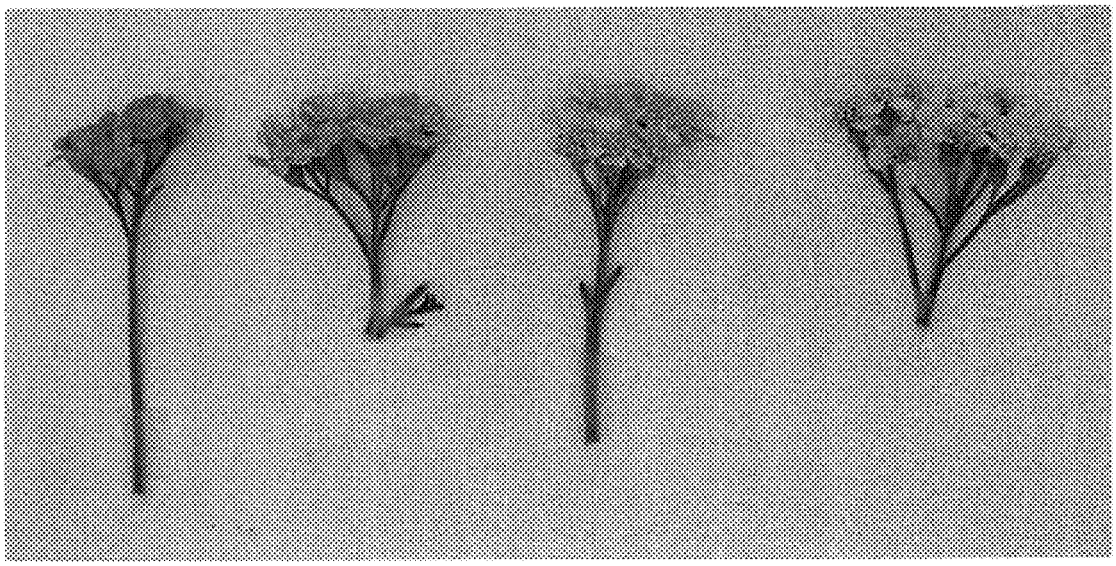

The photograph in FIG. 3 shows the progression of flower color with the newly opened flowers on the left and more mature flowers towards the right.

The colors in the photographs are as close as possible with the photographic and printing technology utilized. The color values cited in the detailed botanical description accurately describe the colors of the new *Achillea.*

DETAILED BOTANICAL DESCRIPTION

The following is a detailed description of the new cultivar as grown outdoors in for 12 weeks from a liner. The descriptions are based on observations over a period of two years in Lacaster, Pa. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Wonderful Wampee' is a cultivar of *Achillea millefolium.*

Parentage: Selection from *Achillea millefolium* 'Summer Pastels' (seed strain).

General description:

*Blooming period.*—Blooms for about 5 weeks, typically from late June through July in Lancaster, Pa.

*Plant habit.*—Herbaceous perennial, upright, mounded habit, strong flowering stems emerge from a basal rosette of foliage.

*Height and spread.*—Matures to about 38 cm in full bloom height and about 58 cm in width.

*Hardiness.*—U.S.D.A. Zones 4 to 8.

*Culture.*—Tolerant to a wide range of growing conditions, growing best in full sun in well-drained, moderately fertile soils.

*Diseases and pests.*—No susceptibility or resistance to diseases or pests common to *Achillea millefolium* has been observed for 'Wonderful Wampee'.

*Root description.*—Fibrous.

Growth and propagation:

*Propagation.*—Basal stem cuttings.

*Root initiation.*—Basal stem cuttings 8 cm in length dipped in 1000 ppm IBA and placed under mist root in about 10 days in a greenhouse kept at about 70° F. without supplemental lighting in spring and summer.

*Time required for root development.*—Rooted cuttings fully develop a 72-cell in about 4 weeks at 70° F. under mist, cells fully develop and flower in a six inch container in about 12 to 13 weeks when grown outdoors under natural lighting or when grown in a greenhouse at 68° F. without supplemental lighting and a constant liquid feed of 150 ppm N.

*Vernalization.*—Not required, vernalized plants flower about 3 weeks sooner but unvernalized plants had better branching with more flowers.

*Crop maintenance.*—Plants can be cut back after the initial flush of flowers and rebloom occurs in about 4 weeks.

*Growth rate.*—Vigorous.

Stem description:

*Shape.*—Round, solid.

*Stem color.*—144B, vertical ridges 144A to 144B.

*Stem size.*—About 3 to 5 mm in diameter, main branch about 35 cm in length.

*Stem surface.*—Glabrous with fine white hairs and numerous vertical ridges.

*Branching habit.*—Main branches emerge from tuft of basal foliage, typically 2 secondary branches emerge from nodes near apex, secondary branches about 10 to 11 cm in length, about 2 mm in diameter, smaller flowering branches emerge from lower nodes after terminal flower heads open.

*Internode length.*—About 5 to 7 cm on the basal region of flowering stem to 1.5 to 3 cm on distal portion of stem.

Foliage description:

*Leaf division.*—Simple, deeply dissected.

*Leaf shape.*—Primarily lanceolate, occasionally oblanceolate.

*Leaf base.*—Blunt.

*Leaf apex.*—Acute.

*Leaf margin.*—Dissected.

*Leaf venation.*—Only midrib is visible, similar to leaf color or lighter 144C to 144D.

*Leaf attachment.*—Sessile, clasping.

*Leaf arrangement.*—Basal foliage and irregularly opposite on flowering stems.

*Leaf surface.*—Glabrous, upper and lower surfaces.

*Leaf color.*—Newly emerged basal foliage; upper and lower surfaces 144C, mature and emerging flowering stem foliage; upper and lower surfaces 137A.

*Leaf size.*—Up to 24 cm in length, up to 5 cm in width, parted segments are up to 3 cm in length and 1 cm in width.

*Foliage fragrance.*—None detected.

Flower description:

General description:

*Type.*—Compound corymb composed of numerous, capitulate, heterogamous with ray florets around the head margin and disk florets in the center, forming a radiant head.

*Lastingness of inflorescence.*—About 7 to 10 days until senescence of ray florets. Bracts and disk florets are persistent.

*Fragrance.*—None detected.

*Quantity of inflorescences.*—Free flowering, about 80 individual corymbs per flowering stem with about 20 to 40 capitula per individual corymb, and about 200 individual corymbs per flowering plant.

*Corymb size.*—Average of 8 cm in width and 6 cm in height for terminal corymbs, average of 4.5 cm in width and height for side corymbs.

*Capitulum buds.*—About 4 mm in height and 2 mm in diameter, shape is ovate, color 139C with colored apex emerging 155B, changing to 155B tips with tips of buds N74C.

*Capitulum color.*—Overall color changes as ray floret color changes; general appearance changes from red-purple (N74 C to N74D) to light purple (77C) to pale pink (69D). Overall effect in full bloom is light pink.

*Capitulum size.*—About 8 mm in width and height.

*Peduncle.*—About 1 to 4 cm in length and 2 mm in diameter, 144A in color, texture is glabrous.

*Pedicel.*—About 5 to 7 mm in length and 1 mm in diameter, 144B in color, texture is glabrous.

*Receptacle.*—Not distinct, small, chaffy, 144A in color.

*Involucral bracts.*—Composed of a series of overlapping bracts, collectively 144B in color and form a cup (calyx-like) about 3 cm in width and 4 cm in height, individual bracts; about 3 mm in length, 1 mm in width, membranous, lanceolate in shape, acute apex, blunt base.

Ray florets (female):

*Number.*—6.

*Shape.*—Orbicular portion on tube enclosing pistil.

*Aspect.*—Held flat, recessed ridges run the length of the orbicular portion from the notches.

*Size.*—6 mm in length and 3 mm width, showy, orbicular portion is 3 mm in length and width, tube portion is 3 mm in length and 0.4 mm in width.

*Petal apex.*—Emarginate with 2 notches (tulip-like).

*Petal base.*—Rounded.

*Petal margins.*—Entire, notched at apex.

*Petal texture.*—Glabrous.

*Color.*—Upper and lower surfaces of petal: tube portion is 144B throughout development and not visible, showy orbicular portion changes from red-purple (N74C) to light purple (77C) to pale pink (69D) as the flowers mature.

Disk florets (bisexual):

*Quantity.*—About 20, densely packed in center of capitulum.

*Shape.*—Tubular, corolla is fused, flared at apex.

*Size.*—About 3 mm in length and up to 1 mm in width (flare).

*Color.*—Base (tube) is 144B in color, flared portion is translucent effectively 8D (yellow) in mass, effective color fades to 155C as ray flowers fade to light pink.

Reproductive organs:

*Presence.*—Disk florets are perfect, ray florets are carpellate or sterile.

*Gynoecium.*—1 Pistil, bifid stigma, light yellow in color (155B), extends just beyond the flare of disk florets and emerges at the junction of the tube and showy portion of the petal of the ray floret. Ovary is 1 mm in length, 0.5 mm in width, placement is inferior, translucent in color.

*Androcoecium.*—5 stamens, fused into tube surrounding style, 2 mm in length and 0.5 mm in width, translucent, pollen is sparse in abundace or hard to visualize and 15D in color.

*Fruit and seed.*—Fruit and seed set has not observed under the conditions tested.

I claim:

1. A new and distinct cultivar of *Achillea* plant named 'Wonderful Wampee' as herein illustrated and described.

* * * * *

UNITED STATES PATENT AND TRADEMARK OFFICE

CERTIFICATE OF CORRECTION

PATENT NO. : PP 18,760 P3
APPLICATION NO. : 11/348942
DATED : April 29, 2008
INVENTOR(S) : Michiel Zwaan It is certified that error appears in the above-identified patent and that said Letters Patent is hereby corrected as shown below:

On the Title Page, Item (75) should be

1. Correct Inventor's name: Michiel Zwaan (Incorrectly listed on Issue Notice as Michiel Zwann)

On the Title Page, Item (75) should be

2. Correct Inventor's address: Alphen aan den Rijn (Incorrectly listed on Issue Notice as Alphen aan den Rikn)

Signed and Sealed this

Twenty-fourth Day of June, 2008

JON W. DUDAS
*Director of the United States Patent and Trademark Office*